(12) United States Patent
Hollander et al.

(10) Patent No.: US 6,648,643 B2
(45) Date of Patent: Nov. 18, 2003

(54) DENTAL IMPLANT/ABUTMENT INTERFACE AND SYSTEM HAVING PRONG AND CHANNEL INTERCONNECTIONS

(75) Inventors: Bruce L. Hollander, Boca Raton, FL (US); Gilbert Ohana, Parkland, FL (US)

(73) Assignee: BioLock International, Inc., Deerfield Beach, FL (US)

( * ) Notice: Subject to any disclaimer, the term of this patent is extended or adjusted under 35 U.S.C. 154(b) by 54 days.

(21) Appl. No.: 10/028,953

(22) Filed: Dec. 19, 2001

(65) Prior Publication Data

US 2003/0113690 A1 Jun. 19, 2003

(51) Int. Cl.[7] ................................................. A61C 8/00
(52) U.S. Cl. ...................................................... 433/173
(58) Field of Search ................................ 433/172, 173, 433/174, 175, 176, 201.1

(56) References Cited

U.S. PATENT DOCUMENTS

| | | | |
|---|---|---|---|
| 5,302,126 A | | 4/1994 | Wimmer et al. |
| 5,449,291 A | * | 9/1995 | Lueschen et al. ............ 433/173 |
| 5,782,918 A | * | 7/1998 | Klardie et al. ................. 606/60 |
| 6,116,904 A | * | 9/2000 | Kirsch et al. ................ 433/173 |
| 6,227,859 B1 | * | 5/2001 | Sutter .......................... 433/173 |
| 6,431,868 B2 | * | 8/2002 | Story .......................... 433/173 |
| 2002/0177105 A1 | * | 11/2002 | Engman ...................... 433/173 |

* cited by examiner

Primary Examiner—Cary E. O'Connor
(74) Attorney, Agent, or Firm—M. K. Silverman

(57) ABSTRACT

A dental implant-abutment interface and assembly comprising an implant, an abutment removably attachable to the implant, and a screw receivable within an axial threaded bore common to both the implant and abutment. The implant includes an elongate body having a proximal end and a distal end, the axial threaded bore open at the proximal end, a radial end surface of a collar comprising the proximal end, and a plurality of axially elongate recesses substantially arcuate in radial cross-section, disposed polarly at the proximal end, and extending distally away from the radial end surface. Each of the arcuate recesses exhibit a curved wall, each having a tangent lying on a common circle disposed inwardly of a circumference of the collar of the implant. The abutment includes the axial threaded bore, a proximal end, and a distal end itself including a collar and prongs projecting distally away from a radial plane at a distal-most axial extent of the collar in which the radial plane is complementally engagable with the radial end surface of the implant. The prongs are disposed equipolarly about the axial bore of the abutment, and each of the prongs are proportioned for engagement with a respective one of the axial recesses of the implant, the axial bore of the abutment communicating with the axial bore of the implant, and the radial surface of the collar having a like radius to that of the radial end surface of the implant. Each of the prongs has a radial cross-section of lesser area than that of its respective implant recess.

14 Claims, 8 Drawing Sheets

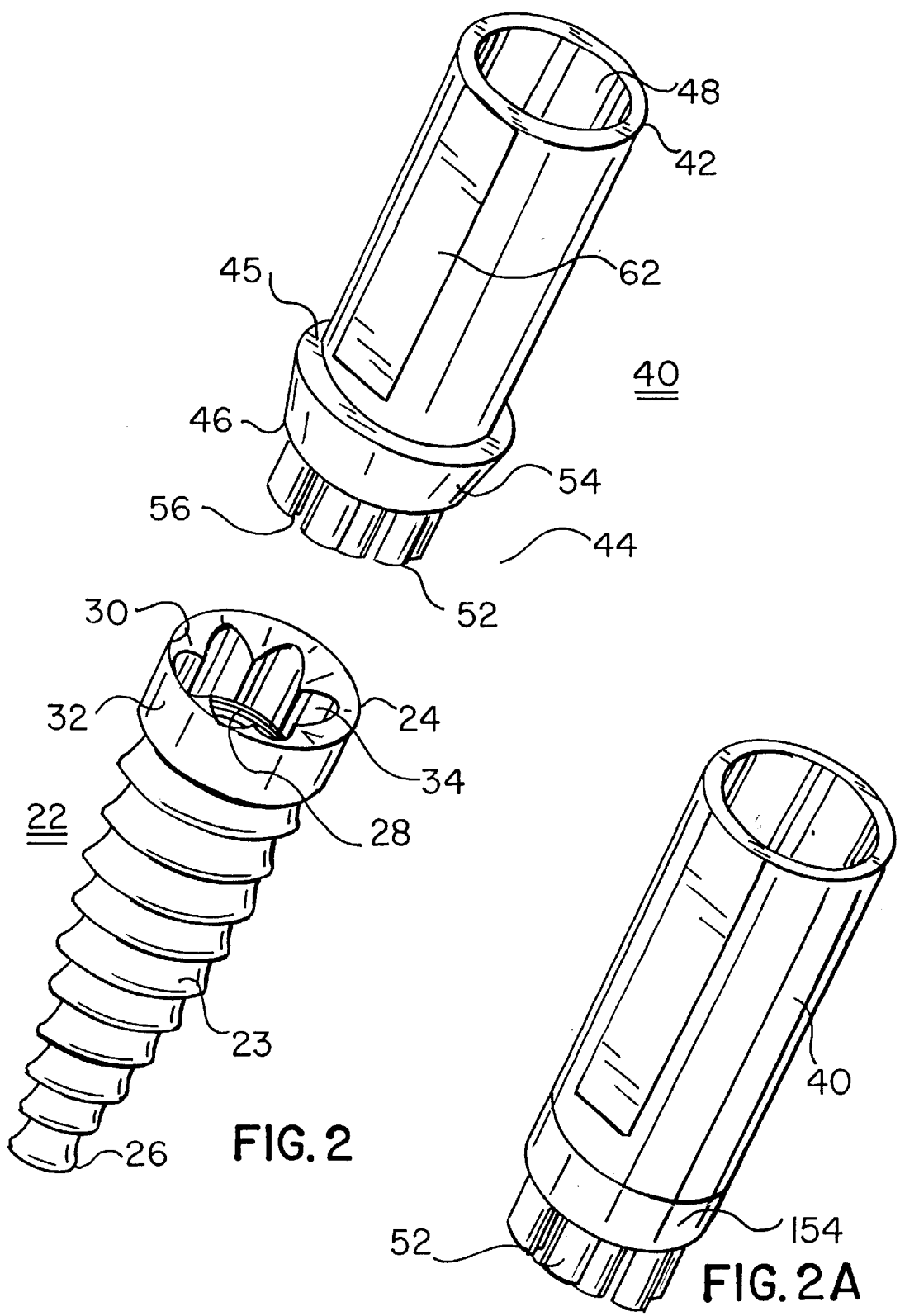

DENTAL IMPLANT/ABUTMENT INTERFACE AND SYSTEM HAVING PRONG AND CHANNEL INTERCONNECTIONS

BACKGROUND OF THE INVENTION

1. Field of the Invention

The instant invention relates generally to dental implants and, more particularly, to a dental implant interface and assembly having an implant portion for securement and osseointegration into an osseotomy site and an abutment portion, securable to the implant portion, for the support of a dental prosthesis.

2. Background and Prior Art

The present invention relates to an improvement over existing spline implant to abutment interfaces as, for example, are reflected in U.S. Pat. No. 5,449,291 (1995) to Lueschen et al, entitled Dental Implant Assembly having Tactile Feedback as well as an improvement of implant/abutment assemblies which employ pin-type interfaces as is reflected in U.S. Pat. No. 5,302,126 (1994) to Wimmer et al, entitled Dental Implant with Adjustable Post. The prior art of Lueschen, and a variant thereof, are shown in FIGS. 1 and 1A. Therein are shown implants 15 and 17 as well as an abutment 19. As may be noted, the male or projecting elements are associated with the implant element, this in distinction to the invention as set forth below, i.e., in which the prongs occur from the abutment, not the implant.

A longstanding concern in the area of implant dentistry has been that of minimizing or eliminating rotation, or the potential therefore, of the abutment portion of the implant system relative to the implant or anchor portion which is embedded within the alveolar bone of the patient. As such, in all implant systems, it is imperative to provide resistance to rotation and, as well, provide for accurate radial, polar and axial indexing of the abutment portion relative to the implant portion. An additional requirement of attachment of the abutment to the implant is termed "tactile feedback," that is, the feeling provided to the hand of the clinician as the abutment is seated with the implant portion. That is, during assembly of the abutment to the implant, it is important for tactile feedback to clearly indicate that the abutment is fully seated in the implant before a securing screw is tightened. As such, implant systems in the prior art that address anti-rotation to the exclusion of tactile feedback will often result in a mis-seating of the abutment relative to the implant. Conversely, systems which are primarily concerned with tactile feedback often result in an implant-to-abutment interface which lacks long-term rotational stability. The instant invention therefore provides an optimization of these otherwise competing objectives in the prior art of abutment-implant interfaces.

SUMMARY OF THE INVENTION

The invention relates to a dental implant-abutment interface and assembly comprising an implant, an abutment removably attachable to the implant, and a screw receivable within an axial threaded bore common to both said implant and abutment. More particularly, said implant includes an elongate body having a proximal end and a distal end, said axial threaded bore open at said proximal end, a radial end surface of a collar comprising said proximal end, and a plurality of axially elongate recesses substantially arcuate in radial cross-section, disposed polarly at said proximal end, and extending distally away from said radial end surface. Each of said arcuate recesses exhibit a curved wall, each having a tangent lying on a common circle disposed inwardly of a circumference of said collar of said implant. Said abutment includes said axial threaded bore, a proximal end, and a distal end itself comprising collar and prongs projecting distally away from a radial plane at a distal-most axial extent of said collar in which said radial plane is complementally engagable with said radial end surface of said implant. Said prongs are disposed equipolarly about said axial bore of the abutment, and each of said prongs are proportioned for engagement with a respective one of said axial circular recesses of said implant, said axial bore of the abutment communicating with the axial bore of said implant, and said radial surface of said collar having a like radius to that of said radial end surface of said implant. Each of said prongs has a radial cross-section of lesser area than that of its respective implant circular recess. The axial bore of said abutment is provided with a screw head-engaging internal shoulder upon which a head of the screw rests after the length thereof complementally engages said threaded bore of the implant.

It is an object of the instant invention to provide a dental implant assembly including an implant portion and an abutment wherein the abutment resists rotation relative to the implant and is radially indexable relative thereto.

It is another object to provide a dental implant/abutment interface having prong and circular channel interconnections to both provide accurate indexing and piloting of the abutment prior to full engagement with the implant.

It is a further object of the invention to provide an implant/abutment interface which provides tactile feedback to the clinician while also providing resistance to rotation after osseointegration of the implant into the alveolar bone of the patient.

It is a still further object to obtain an interface and assembly of the above type wherein interconnecting prongs thereof may fail as a result of over-torquing of the abutment without damage to the implant or failure of the implant-abutment interface, and in which indexing of the prongs can be reset within the implant to either continue to screw the implant into the bone or to remove the implant from such bone, thereby providing a fail-safe feature to the implant clinician not withstanding such prong failure The above and yet other objects and advantages of the present invention will become apparent from the hereinafter set forth Brief Description of the Drawings and Detailed Description of the Invention as set forth herein.

BRIEF DESCRIPTION OF THE DRAWINGS

FIG. 2 is an exploded view showing the implant and abutment elements of the present invention. Therein, the prongs are on the abutment, which the implant has circular recesses.

FIG. 2A is an enlarged view of an alternative collar structure for the abutment element.

DETAILED DESCRIPTION OF THE INVENTION

Figure 3:
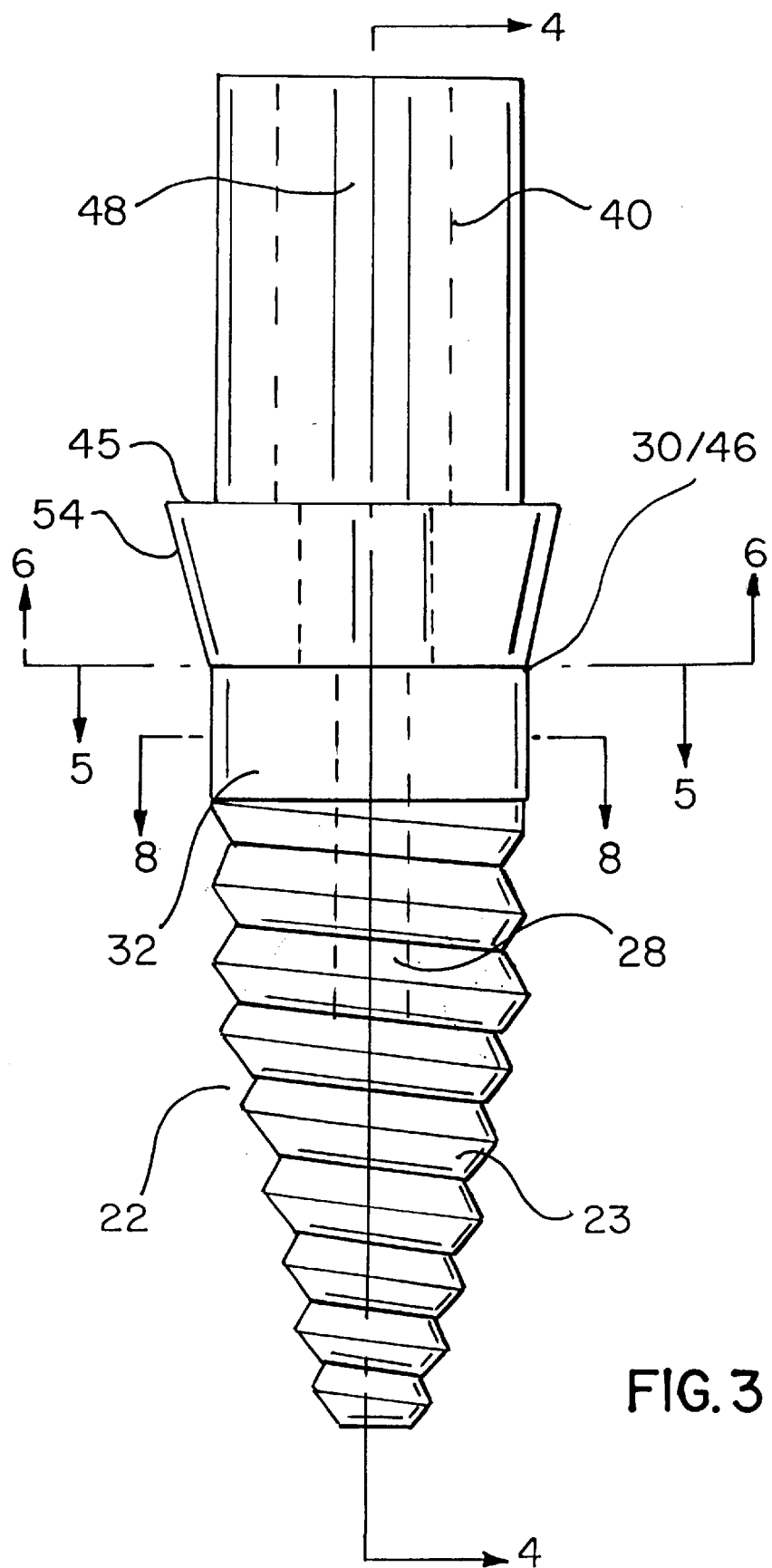
FIG. 3 is an assembly view of the elements of FIG. 2.

With reference to the exploded view of FIG. 2, the inventive dental implant-abutment interface and assembly may be seen to include an implant 22 and an abutment 40. The implant, which is adapted for insertion into an osseotomy site, includes an elongate body 23 having a proximal end 24, a distal end 26, and an axial threaded bore 28 which is open at said proximal end 24 of the implant. At said opening is defined a radial surface 30 as well as a collar 32. As is shown in FIG. 3, collar 32 typically comprise a cylindrical segment 31. In another embodiment, collar 32 may taper outward in the direction of said implant body 23.

Between the beginning of threads of threaded bore 28 and said radial surface 30 are a circumferential plurality of axially elongate recesses 34 (see also FIG. 5), each of which are substantially arcuate in radial cross-section and, as well, are disposed equipolarly about a longitudinal axis of said threaded bore 28 of the implant 22. As may be further noted, said recesses 34 extend axially away from said radial surface 30 and extend downwardly (distally) in the implant to the extent of said collar 32 (see also FIG. 4).

Figure 5:
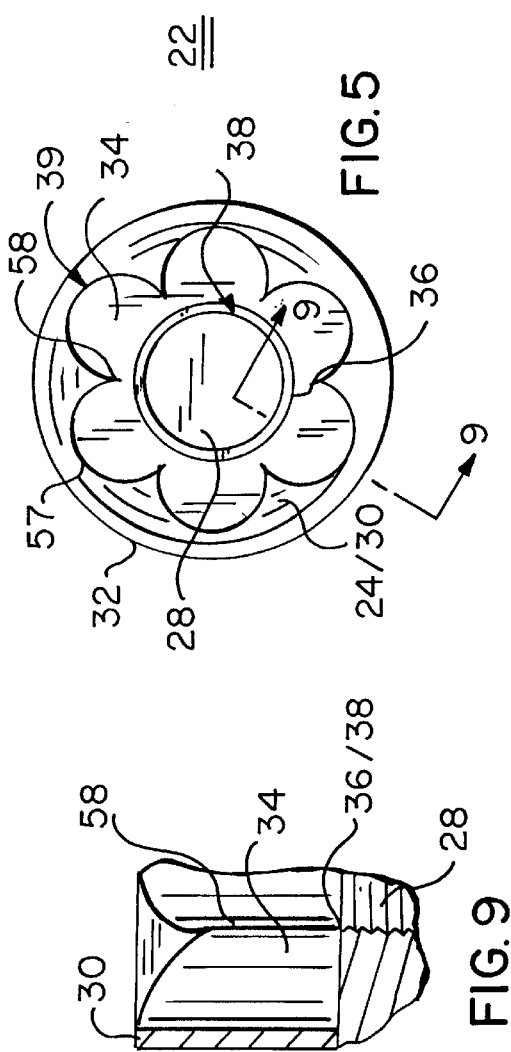
FIG. 5 is a radial cross-sectional view taken through Line 5—5 of FIG. 3 showing the appearance of the proximal end of the implant.

As may be noted with reference to FIG. 5, each of said recesses 34 exhibit a curved innermost wall 36 which lies upon a common circle 38 radially disposed slightly beyond a circumference which defines the opening of said bore 28. Further, an outermost radius 39 of each recess 34 lies upon a common circle which is disposed slightly inwardly of the circumference of said radial surface 30 of the implant.

Figure 4:
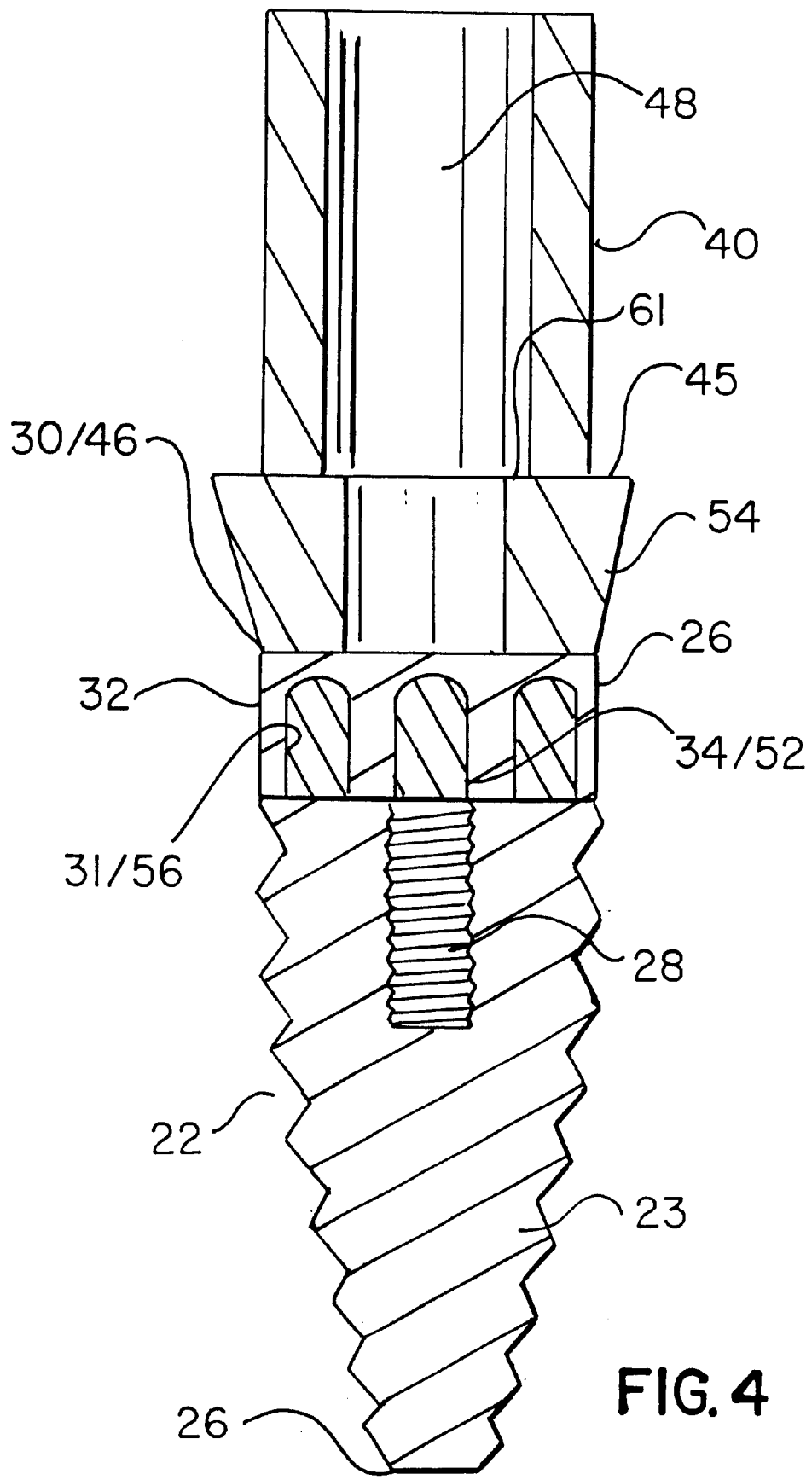
FIG. 4 is an axial cross-sectional view taken through Line 4—4 of FIG. 3.
Figure 4A:
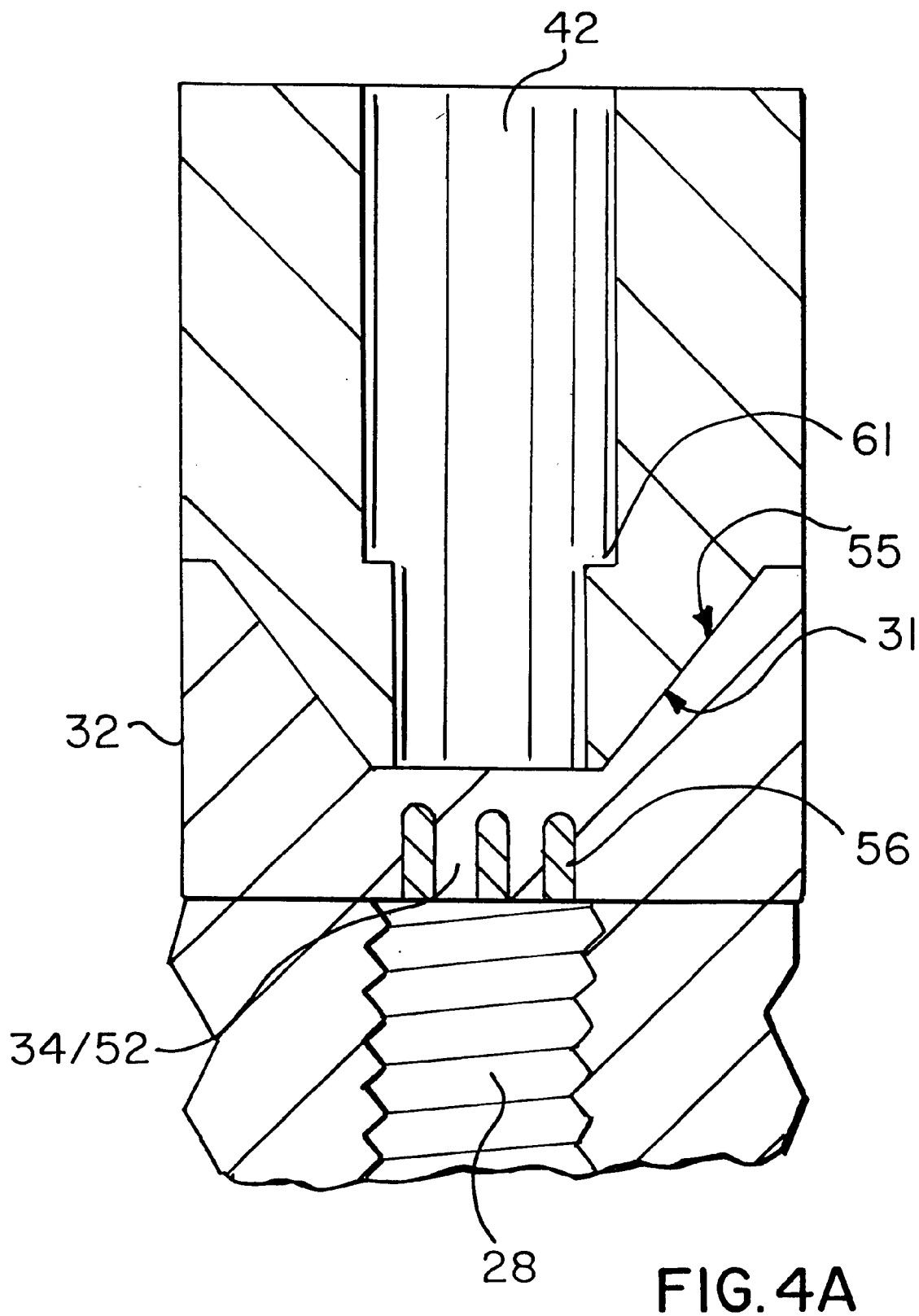
FIG. 4A is a view similar to that of FIG. 4, however showing a conical end surface interface between the implant and abutment elements.
Figure 7:
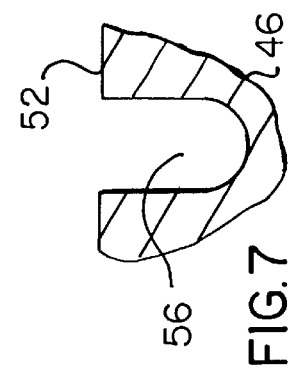
FIG. 7 is a cross-sectional view taken through Line 7—7 of FIG. 6.
Figure 12:
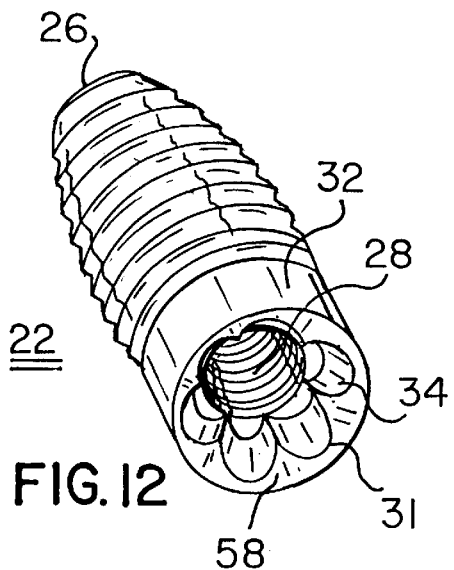
FIG. 12 is a diagonal perspective view of the implant element of the embodiment of FIG. 4A.
Figure 11:
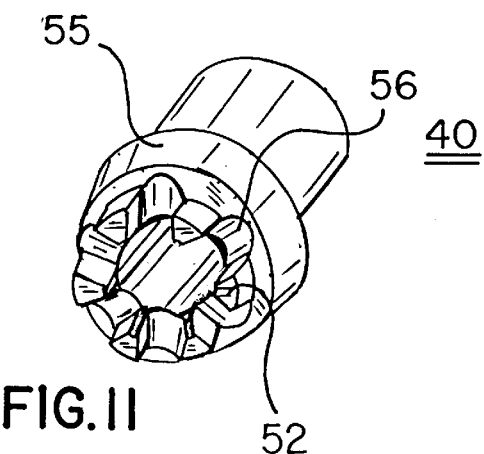
FIG. 11 is a diagonal perspective view of the element of FIG. 10.

As may be noted in FIGS. 4A and 12, said radial surface may comprise a tapered radial surface 31.

With further reference to the exploded view of FIG. 2, the inventive system may be seen to further include said abutment 40 which, as in the case of all dental system abutments, is adapted for the support of a tooth prosthesis. Said abutment 40 includes a proximal end 42, a distal end 44, an annular shoulder 45 54, an axial bore 48, a distally tapered collar 54 beginning at the axial location of said annular shoulder 45 and continuing to the axial position of a virtual radial plane 46. Optionally, a cylindrical shoulder 154 (see FIG. 2A) can be employed. Distally depending from said virtual plane 46 of said collar 54 or 154 are projecting prongs 52 which, together with said virtual radial plane 46, are proportioned for engagement within said axial recesses 34 and said radial surface 30 or 31 which defines the proximal-most axial extent of said implant 22.

Figure 1:
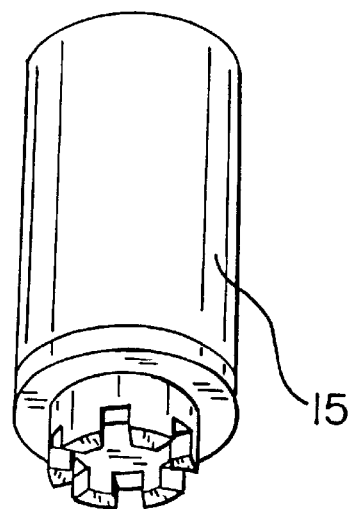
FIGS. 1 and 1A are perspective views of prior art spline-type implant-abutment assemblies. Therein, prongs are on the implants, not the abutment, while the abutment has channeled grooves.
Figure 1A:
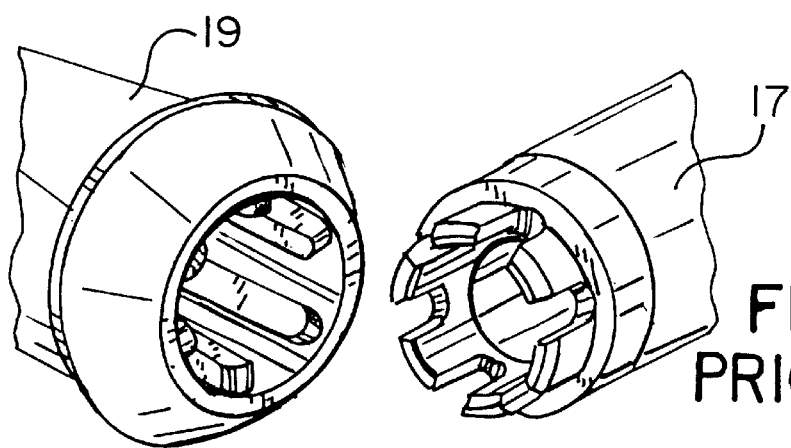
Figure 6:
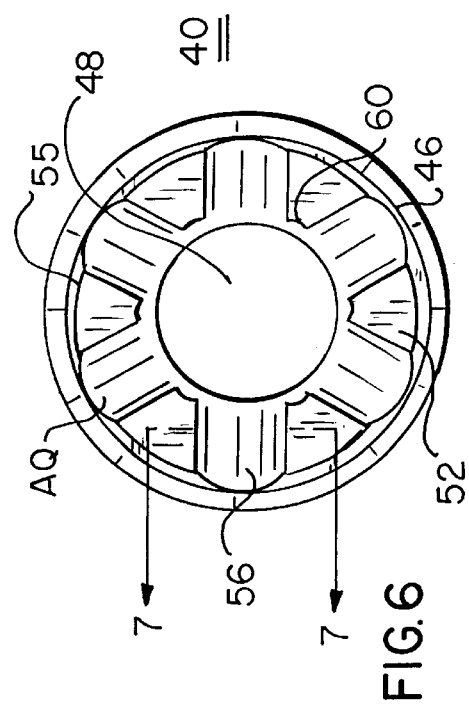
FIG. 6 is a radial cross-sectional view taken through Line 6—6 of FIG. 3 showing the appearance of the distal-most end of the abutment, including the prongs thereof.
Figure 9:
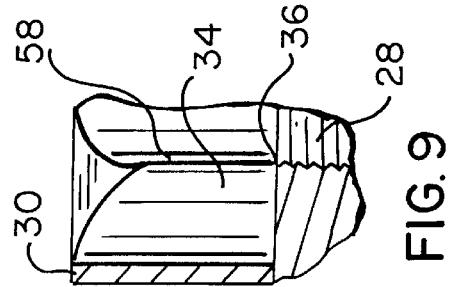
FIG. 9 is a partial radial cross-sectional view taken through Line 9—9 of FIG. 5.
Figure 8:
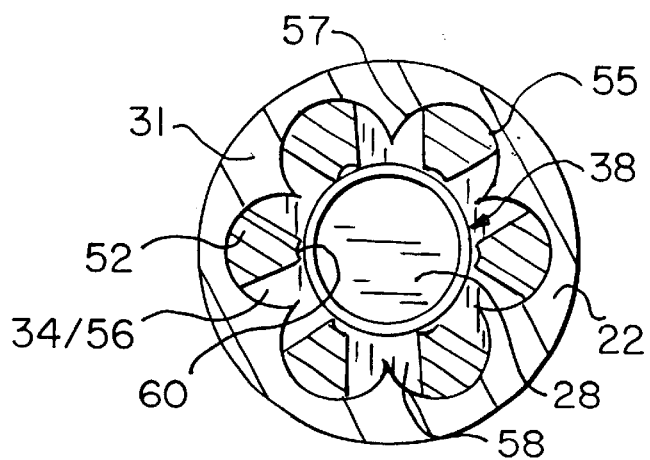
FIG. 8 is a radial cross-sectional view of the implant and abutment prongs taken through Line 8—8 of FIG. 3
Figure 10:
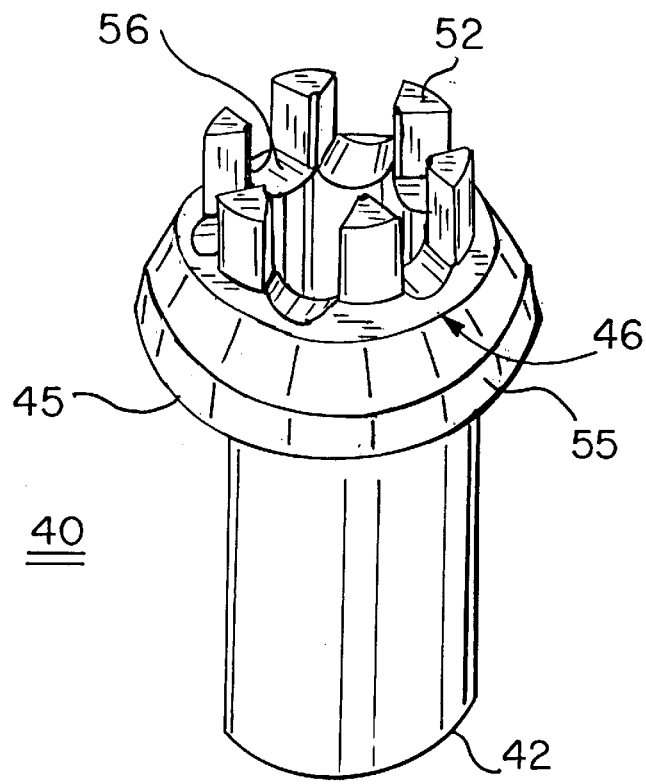
FIG. 10 is an inverted perspective view of the abutment element of the embodiment of FIG. 4A.

As may be noted in the axial cross-sectional view of FIG. 6, said prongs 52 are disposed equipolarly about an axis of abutment bore 48 and are proportioned for engagement of each of said axial circular recesses 34 of the implant, this as may be more fully appreciated with reference to the radial-cross sectional view of FIG. 8. In FIGS. 6 and 8, prongs 52 appear, in radial cross-section, as trapezoids with curved major and minor bases 55 and 60 respectively. Therein, each major base 55 thereof mates with a wall 57 of each elongate recess 34 of the implant 22. However, interdigitaged between said prongs 52 are U-shaped regions 56 (see FIGS. 2, 4 and 10) which slip over intersections 58 (see FIGS. 2, 5, 8 and 9) of curved surfaces 57 of said recesses 34. As such, prongs 52, when fully inserted within recesses 34 of the implant, appear in the manner shown in FIGS. 4 and 8. That is, curved major base 55 of each prong 52 mates with curved wall 57 of each recess, and minor base 60 of each prong 52 contacts a wall of the circumference 38 of implant bore 28. As may be further noted with reference to FIGS. 4 and 6, the polar dimension of each U-shaped channel 56 will typically exceed that of the polar dimension (as defined by major base 55) of each prong 52. The invention therefore differs materially from the prior art (see FIG. 1) and, as described in the Background of the Invention, with reference to both the polar and radial extent and geometry of the prongs of the abutment relative to recesses complemental thereto. The special-purpose radial geometry of the interlock between male and female elements is more particularly shown in the view of FIGS. 4 and 8. It is to be appreciated that recesses 34 of the implant will not be entirely filled by the geometry of prongs 52 but, rather, are held in place through (a) the interdigitating interlock of channels 56 with curved surface intersections 58 of the implant and (b) the interlock between said prongs 52 and, particularly, major bases 55 with walls 57 of said axial recesses and of each prong minor base 60 with circumference 38 of the opening of the implant bore 28.

Figure 8A:
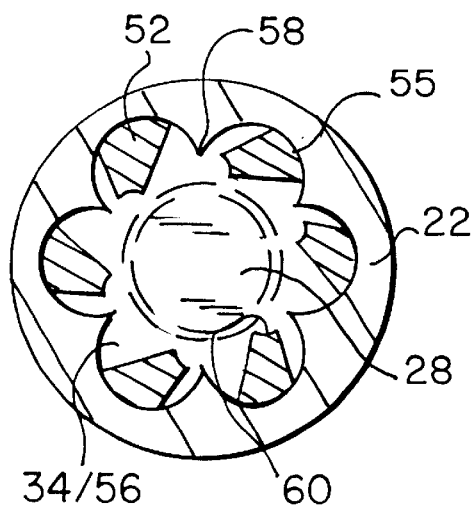
FIG. 8A is a view similar to that of FIG. 8, however showing the appearance of the prongs in the event of overtorquing of the abutment.

With reference to FIG. 8A, there is yet further noted that the difference in cross-sectional area between the prongs of the abutment and the recesses of the implant allows the prongs to fail when over-torqued, without fatally damaging the implant or the implant abutment interface, so that the prongs can be reset in the implant and will continue to engage, allowing the clinician to either continue to screw the implant into the bone or may remove the implant from the bone. This fail-safe feature is an important factor in implant dentistry.

After assembly of the elements in the manner shown in FIGS. 3, 4 and 8, a screw (not shown) is placed within both communicating abutment bore 48 and implant bore 28 to both secure the implant and abutment to each other and, as well, to provide a platform upon which the tooth prosthesis may be secured. Also shown is shoulder 61 of bore 48 upon which the screw head rests.

Further shown in the view of FIG. 2 is a flat lateral surface 62 of the abutment having utility in the rotation of the abutment relative to the implant after the complemental elements thereof have been inserted into each other, this to create a cam-lock action A further distinguishing feature of the instant system is that of said collar 54 of the abutment tapers to a diameter equal to the diameter of implant collar 32 at the plane of contact with said radial surface 30 or 31 thereof. It has been found that such a collar provides enhanced strength and stability to the resultant system. In FIG. 4A is shown the conical interface of implant-tapered surface 31 with abutment-tapered surface 55.

Figure 13:
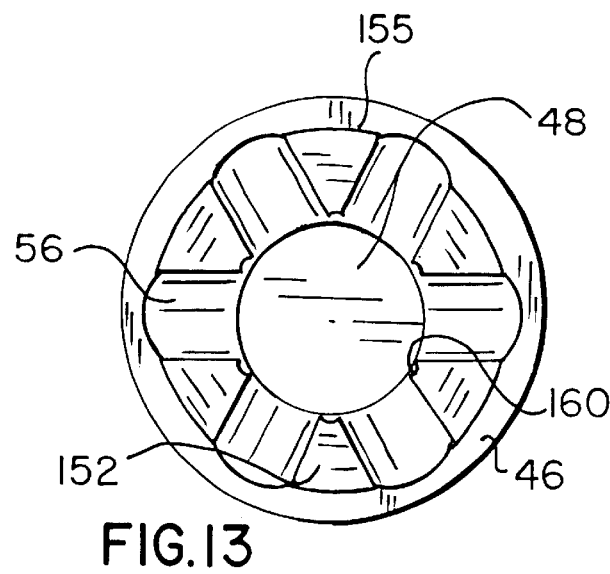
FIG. 13 is a view, similar to that of FIG. 8, showing a further embodiment of the abutment elements.

It is to be further understood that a triangular cross-sectional geometry of prongs 152 may be utilized in lieu of the above trapezoidal geometry of prongs 52. See FIG. 13. In such triangular prongs, there would exist apex 160 and curved outer leg 155.

While there has been shown and described the preferred embodiment of the instant invention it is to be appreciated that the invention may be embodied otherwise than is herein specifically shown and described and that, within said embodiment, certain changes may be made in the form and arrangement of the parts without departing from the underlying ideas or principles of this invention as set forth in the claims appended herewith.

We claim:

1. A dental implant-abutment interface and assembly, comprising:

(a) an implant for insertion into an osseotomy site, said implant including an elongate body having a proximal end and a distal end, an axial threaded bore open at said proximal end, a radial end surface of a collar comprising said proximal end, and a plurality of axially circular recesses substantially arcuate in radial cross-section and disposed equipolarly about said threaded bore at said proximal end and extending distally away from said flat radial surface, each of said recesses include a curved outer wall having a tangent with common circle disposed inwardly of a circumference of said implant;

(b) an abutment removably attachable to said implant for supporting a tooth prosthesis, said abutment including an axial bore, a proximal end, and a distal end comprising (i) a collar; and (ii) prongs projecting distally from a radial plane at a distal-most axial extent of said collar, said plane complementally engagable with said radial end surface of said implant, said prongs disposed equipolarly about said axial bore of said abutment, each of said prongs proportioned for engagement with a respective one of said axial recesses of said implant in which an area of radial cross-section defined by each of said prongs is less than an area of radial cross-section, at a like axial position, of said respective each one of said axial recesses with which said each prong is engaged, said axial bore of said abutment communicating with said axial bore of said implant, said radial plane of said collar having a like radius to that of said radial end surface of said implant; and (c) a screw, receivable in said axial bore and upon a screw head-engaging internal shoulder of said abutment, and having screw threads complementally engagable with said threaded bore of said implant.

2. The assembly as recited in claim 1, in which said prongs of said abutment each define a substantially trapezoidal radial cross-section having major and minor bases.

3. The assembly as recited in claim 2, in which each minor base of said cross-section lies upon a common circle contiguous to a circumference of said bore of said abutment.

4. The assembly as recited in claim 3, in which each major base of each prong cross-section lies upon a common circle contiguous to an outermost circumference of said radial plane of said abutment collar.

5. The assembly as recited in claim 4, in which said prongs are separated by equipolar axially U-shaped interdigitating channels falling within the curvature of said common circle in which each polar dimension of said interdigitating channels exceeds each polar dimension defined by said curved outer base of each of said trapezoidal cross-section of said prongs.

6. The assembly as recited in claim 5, which said major and minor bases are each curved.

7. The assembly as recited in claim 1, in which an exterior surface of said implant comprises a tapered buttress thread geometry.

8. The assembly as recited in claim 1, in which radial cross-sections of said prongs of said abutment each substantially define a triangle.

9. The assembly as recited in claim 8, in which vertices of said substantially triangular radial cross-sections of said prongs comprise rounded surfaces.

10. The assembly as recited in claim 1, in which said radial end surface of said implant and said radial plane of said abutment each define a section of a cone and are complemental to each other.

11. The assembly as recited in claim 10, which said prongs of said abutment each define a substantially trapezoidal radial cross-section having curved major and minor bases.

12. The assembly as recited in claim 10, in which said abutment collar comprises an annular collar tapering distally toward said radial plane of said abutment.

13. The assembly as recited in claim 10, in which in which said prongs of said abutment each define a substantially trapezoidal radial cross-section having major and minor bases.

14. The assembly as recited in claim 13, in which said major and minor bases are each curved.

* * * * *